US010762169B2

(12) United States Patent
Limsopatham et al.

(10) Patent No.: US 10,762,169 B2

(45) Date of Patent: Sep. 1, 2020

(54) SYSTEM AND METHOD FOR DETERMINING SIDE-EFFECTS ASSOCIATED WITH A SUBSTANCE

(71) Applicant: Accenture Global Solutions Limited, Dublin (IE)

(72) Inventors: Nut Limsopatham, Dublin (IE); Md Faisal Zaman, Dublin (IE)

(73) Assignee: Accenture Global Solutions Limited, Dublin (IE)

( * ) Notice: Subject to any disclaimer, the term of this patent is extended or adjusted under 35 U.S.C. 154(b) by 579 days.

(21) Appl. No.: 15/625,702

(22) Filed: Jun. 16, 2017

(65) Prior Publication Data

US 2018/0365380 A1 Dec. 20, 2018

(51) Int. Cl.

| | |
|---|---|
| ***G06F 19/00*** | (2018.01) |
| ***G16H 15/00*** | (2018.01) |
| ***G16H 50/70*** | (2018.01) |
| ***G16H 70/40*** | (2018.01) |
| ***G06F 40/30*** | (2020.01) |

(Continued)

(52) U.S. Cl.

CPC .......... *G06F 19/326* (2013.01); *G06F 40/205* (2020.01); *G06F 40/30* (2020.01); *G16H 15/00* (2018.01); *G16H 50/70* (2018.01); *G16H 70/40* (2018.01); *G06Q 50/01* (2013.01)

(58) Field of Classification Search

CPC .................................................... G06F 19/326

See application file for complete search history.

(56) References Cited

U.S. PATENT DOCUMENTS 7,461,006 B2 * 12/2008 Gogolak ................ G16H 70/40 705/2

2002/0082868 A1 6/2002 Pories et al.

(Continued)

OTHER PUBLICATIONS

Collier, Nigel, et al., "WDCM 2017 Workshop on Mining Online Health Reports," WSDM 2017 Feb. 6-10, 2017, Cambridge, United Kingdom, 2 pgs.

(Continued)

*Primary Examiner* — Robert A Sorey

*Assistant Examiner* — Kristine K Rapillo

(74) *Attorney, Agent, or Firm* — Brinks Gilson & Lione

(57) ABSTRACT

A system for determining adverse effects associated with a substance includes a side-effect recognizer, a relationship extractor, a processor, and a reporting system. The side-effect recognizer utilizes a first recurrent neural network (RNN) to identify a first portion of received data associated with an adverse effect to thereby determine the adverse effect associated with the received data. The relationship extractor utilizes a second RNN to identify a second portion of the received data associated with a substance and a third portion of the received data that indicates a relationship between the substance and the adverse effect to thereby determine the substance associated with the received data and the relationship between the substance and the adverse effect. The processor is in communication with the adverse effect recognizer and the substance relationship extractor and aggregates and relates the adverse effect, substance, and relationship. The reporting system is in communication with the processor and generates a report to convey the relationship between the substance and the adverse effect.

15 Claims, 6 Drawing Sheets

(51) Int. Cl.
*G06F 40/205* (2020.01)
*G06Q 50/00* (2012.01)

(56) References Cited

U.S. PATENT DOCUMENTS

| | | | | |
|---|---|---|---|---|
| 2002/0165853 | A1 | 11/2002 | Gogolak | |
| 2007/0214009 | A1 | 9/2007 | Epstein et al. | |
| 2009/0099870 | A1 | 4/2009 | Wilkinson et al. | |
| 2009/0119095 | A1 | 5/2009 | Beggelman | |
| 2010/0324927 | A1 | 12/2010 | Tinsley | |
| 2013/0041685 | A1 | 2/2013 | Yegnanarayanan | |
| 2013/0073554 | A1 | 3/2013 | Bachert et al. | |
| 2013/0124523 | A1 | 5/2013 | Rogers et al. | |
| 2013/0226616 | A1* | 8/2013 | Nigam | G06Q 10/00 705/3 |
| 2014/0006013 | A1 | 1/2014 | Markatou et al. | |
| 2014/0046696 | A1 | 2/2014 | Higgins | |
| 2014/0058744 | A1 | 2/2014 | Nadarajah et al. | |
| 2015/0081323 | A1 | 3/2015 | Jackson et al. | |
| 2016/0048655 | A1 | 2/2016 | Maitra et al. | |
| 2017/0228500 | A1 | 8/2017 | Massengale | |
| 2017/0293725 | A1 | 10/2017 | Liu et al. | |
| 2017/0329900 | A1 | 11/2017 | Kato et al. | |
| 2017/0351830 | A1 | 12/2017 | Burger et al. | |
| 2018/0082197 | A1 | 3/2018 | Aravamudan | |
| 2018/0089381 | A1 | 3/2018 | Allen et al. | |
| 2018/0089568 | A1 | 3/2018 | Allen | |
| 2018/0101598 | A1 | 4/2018 | Allen et al. | |
| 2019/0005019 | A1 | 1/2019 | Burke et al. | |

OTHER PUBLICATIONS

Limsopatham, Nut, et al., "Normalising Medical Concepts in Social Media Texts by Learning Semantic Representation," *Proceedings of the 54th Annual Meeting of the Association for Computational Linguistics*, Berlin, Germany, Aug. 7-12, 2016, © 2016 Association for Computational Linguistics, pp. 1014-1023.

Limsopatham, Nut, et al., "Learning Orthographic Features in Bi-directional LSTM for Biomedical Named Entity Recognition," *Proceedings of the Fifth Workshop on Building and Evaluating Resources for Biomedical Text Mining* (*BioTxtM 2016*), Osaka, Japan, Dec. 12, 2016, pp. 10-19.

Limsopatham, Nut, et al., "Towards the Semantic Interpretation of the Personal Health Messages from Social Media," *CIKM'15*, Oct. 19-23, 2015, Melbourne, Australia, 4 pgs.

* cited by examiner

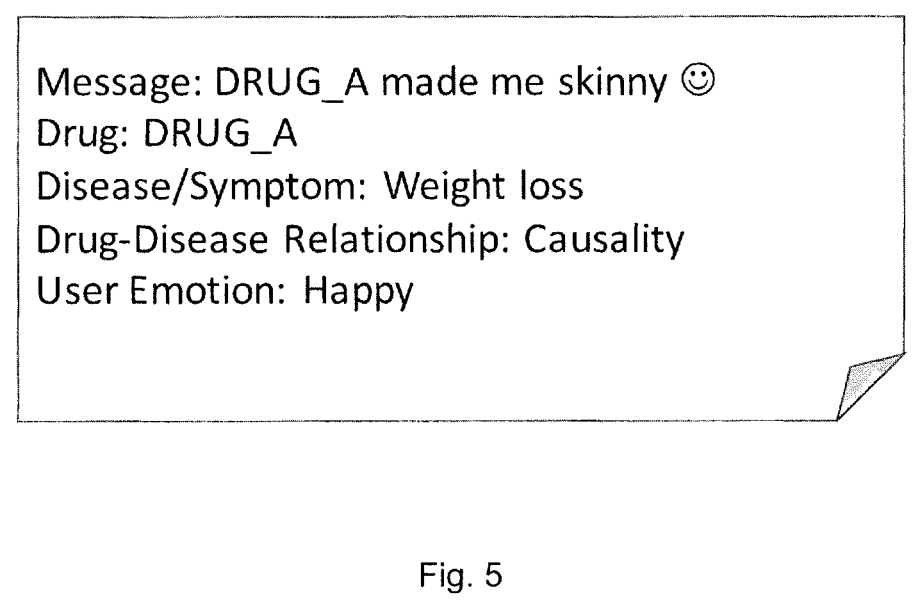

Message: DRUG_A made me skinny ☺
Drug: DRUG_A
Disease/Symptom: Weight loss
Drug-Disease Relationship: Causality
User Emotion: Happy

Fig. 5

SYSTEM AND METHOD FOR DETERMINING SIDE-EFFECTS ASSOCIATED WITH A SUBSTANCE

BACKGROUND

Field

This application generally relates to natural language processors. In particular, this application describes a system and method for determining side-effects associated with a substance using various natural language processors.

Description of Related Art

In the context of substances such as drugs, side-effects are typically considered effects felt by a patient other than to the intended/therapeutic effect. Some side-effects may be adverse. Many countries require drug companies to report these adverse effects. Drug companies typically conduct extensive research and perform clinical trials to identify potential side-effects.

However, the reliability of the clinical trials may be lacking due to the limited number of patients partaking in the clinical trials. For example, the number of patients involved in the clinical trial may be relatively low and selected to simply comply with a regulatory requirement.

Moreover, once a drug has been approved and released the public, the drug companies' ability to track side-effects is diminished. For example, drug companies may have to rely on health care professionals, busy with other tasks, to provide any information related to side-effects.

BRIEF SUMMARY

In one aspect, a system for determining adverse effects associated with a substance includes a side-effect recognizer, a relationship extractor, a processor, and a reporting system. The side-effect recognizer is configured to identify a first portion of received data associated with an adverse effect to thereby determine the adverse effect associated with the received data. The relationship extractor is configured to identify a second portion of the received data associated with a substance and a third portion of the received data that indicates a relationship between the substance and the adverse effect to thereby determine the substance associated with the received data and the relationship between the substance and the adverse effect. The processor is in communication with the side-effect recognizer and the substance relationship extractor and aggregates and relates the adverse effect, substance, and relationship. The reporting system is in communication with the processor and generates a report to convey the relationship between the substance and the adverse effect.

In a second aspect, a non-transitory computer readable medium includes instruction code that facilitates determining adverse effects associated with a substance. The instruction code is executable by a machine for causing the machine to control a first recurrent neural network (RNN) to identify a first portion of received data associated with an adverse effect to thereby determine the adverse effect associated with the received data, and to control a second RNN to identify a second portion of the received data associated with a substance and a third portion of the received data that indicates a relationship between the substance and the adverse effect to thereby determine the substance associated with the received data and the relationship between the substance and the adverse effect. The instruction code is also executable by the machine to cause the machine to aggregate and relate the adverse effect, substance, and relationship, and generates a report to convey the relationship between the substance and the adverse effect.

In a third aspect, a method for determining adverse effects associated with a substance includes identifying, by a first recurrent neural network (RNN), a first portion of received data associated with an adverse effect to thereby determine the adverse effect associated with the received data, and identifying, by a second RNN, a second portion of the received data associated with a substance and a third portion of the received data that indicates a relationship between the substance and the adverse effect to thereby determine the substance associated with the received data and the relationship between the substance and the adverse effect. The method also includes aggregating and relating the adverse effect, substance, and relationship, and generating a report to convey the relationship between the substance and the adverse effect.

BRIEF DESCRIPTION OF THE DRAWINGS

FIG. 5 illustrates an exemplary grouping of information associated with the phrase retrieved from the social media source.

DETAILED DESCRIPTION

The embodiments describe below overcome the problems described in the background by providing a system that is able to retrieve comments posted by users on various social media services, parse the comments to determine whether the comments are related to drug side-effects, and aggregate information in such comments to identify specific side-effects associated with specific drugs. The system is capable of parsing hundreds of thousands of comments in a given day and aggregating the results into a database. By aggregating the results, duplicate entries in the database can be avoided. This in turn results in extremely efficient/reduced memory usage in tracking side-effect information. In addition, for the downloaded social media posts, once they are processed, they will be stored in distributed databases, which facilitates efficient usage/access with limited memory requirement.

Figure 1:
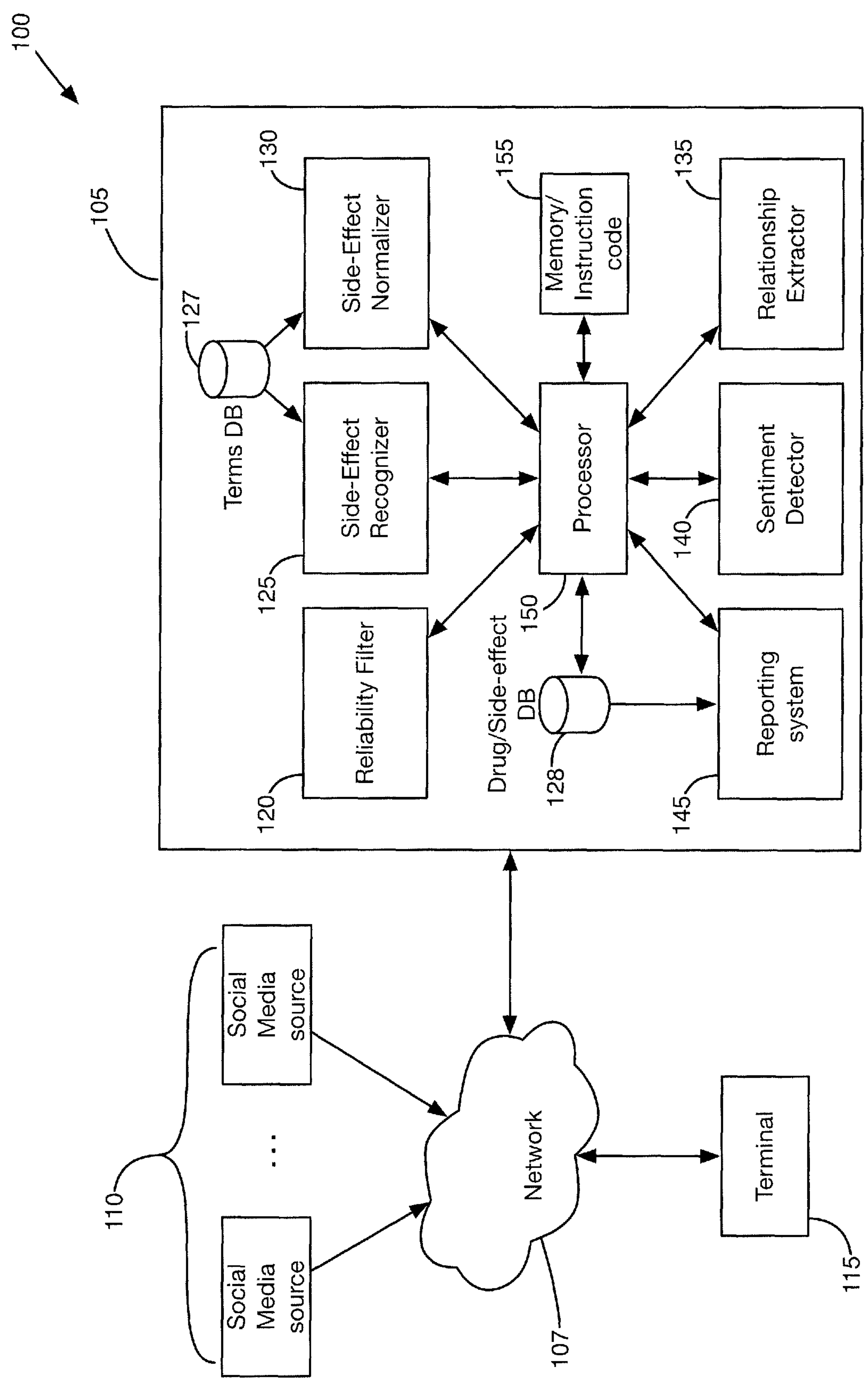
FIG. 1 illustrates an exemplary environment for determining side-effects associated with a substance.

FIG. 1 illustrates an exemplary environment 100 for determining side-effects associated with a substance. Illustrated in the environment 100 are entities that include a side-effect determining system (SEDS) 105, a group of social media sources 110, and a terminal 115. The SEDS, social media source, and terminal 115 may communicate with one another via a network 107, such as the Internet.

The social media sources 110 generally correspond to systems that host social media content. Exemplary social media sources 110 may include Twitter®, Facebook®, Instagram®, etc. Content provided by the social media sources 110 may include public comments posted by users of the social media sources 110, such as a Twitter Tweet. For example, a user may post a comment regarding his experience with a drug/substance, such the comment illustrated in FIG. 3A.

In general the SEDS 105 may crawl the social media sources 110 searching for user comments related to substances and possible side-effects experienced by the user. The SEDS 105 includes various subsystems that facilitate making these determinations that includes a reliability filter 120, a side-effect recognizer 125, a side-effect normalizer 130, a relationship extractor 135, an emotion detector 140, a reporting system 145, and a processor 150 that executed instruction code stored in a memory device 155 for coordinating activities performed between the various subsystems.

It is contemplated that each subsystem may correspond to a stand-alone computer system such as an Intel®, AMD®, or PowerPC® based computer system or a different computer system. The computer systems may include an operating system, such as a Microsoft Windows®, Linux, Unix® or other operating system. It is also contemplated that operations performed on the various subsystems may be combined into a fewer or greater number of subsystems to facilitate speed scaling of the SEDS 105, cost reductions, etc.

Figure 2:
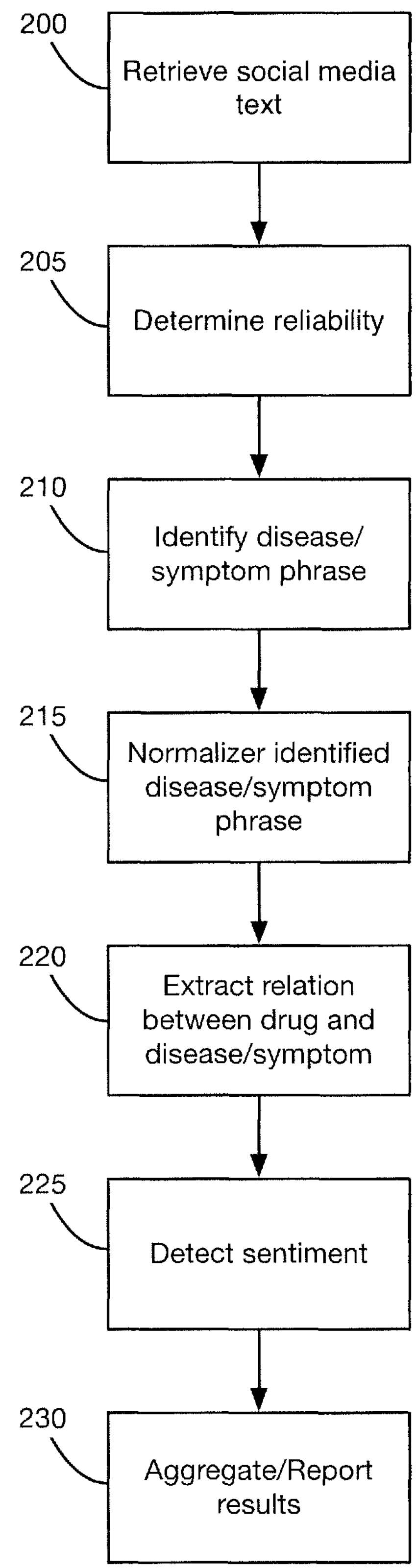
FIG. 2 illustrates operations performed by various entities of the environment.

Operations performed by one or more of the subsystems of the SEDS 105, 100 are illustrated in FIG. 2 and are best understood by referencing FIGS. 3A-5. In this regard, the operations may be implemented via instruction code stored in non-transitory computer readable media that resides within the entities configured to cause the respective entities to perform the operations in the figures.

Figure 3A:
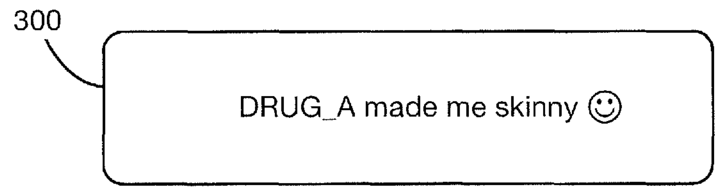
FIG. 3A illustrates an exemplary phrase that may be retrieved from a social media source of the environment.

At block 200, the SEDS 105 may retrieve social media text such as the comment 300 illustrated in FIG. 3A from one of a group of social media sources 110. For example, the SEDS 105 may, via the network 107, monitor websites such as Twitter®, Facebook®, Instagram®, etc. The SEDS 105 may process comments posted by users as they are posted. Alternatively, the SEDS 105 may download any number of comments and process the comments on a periodic basis, such as daily, weekly, etc.

At block 205, the reliability associated with each comment may be determined by the reliability filter 120. The reliability associated with a given comment may be based on the number of followers, retweets, etc., associated with a user. In addition, the reliability associated with a user may have been determined ahead of time, and the reliability filter may have been configured assess comments associated with the user as high reliability comments. The reliability filter 120 may include or implement a support vector machine (SVM). The SVM may correspond to a supervised learning system with associated learning algorithms that analyze data to classify the data as belonging to two or more groups. For example, in this case, the SVM may be trained to classify comments posted by users as reliable or unreliable. In this regard, an SVM classifier of the SVM is trained to distinguish between reliable and unreliable posts by using several types of features, including textual features and social network features (e.g., the numbers of friends/followers in the social media, how many of the posts from the same user are retweeted/liked).

Figure 3B:
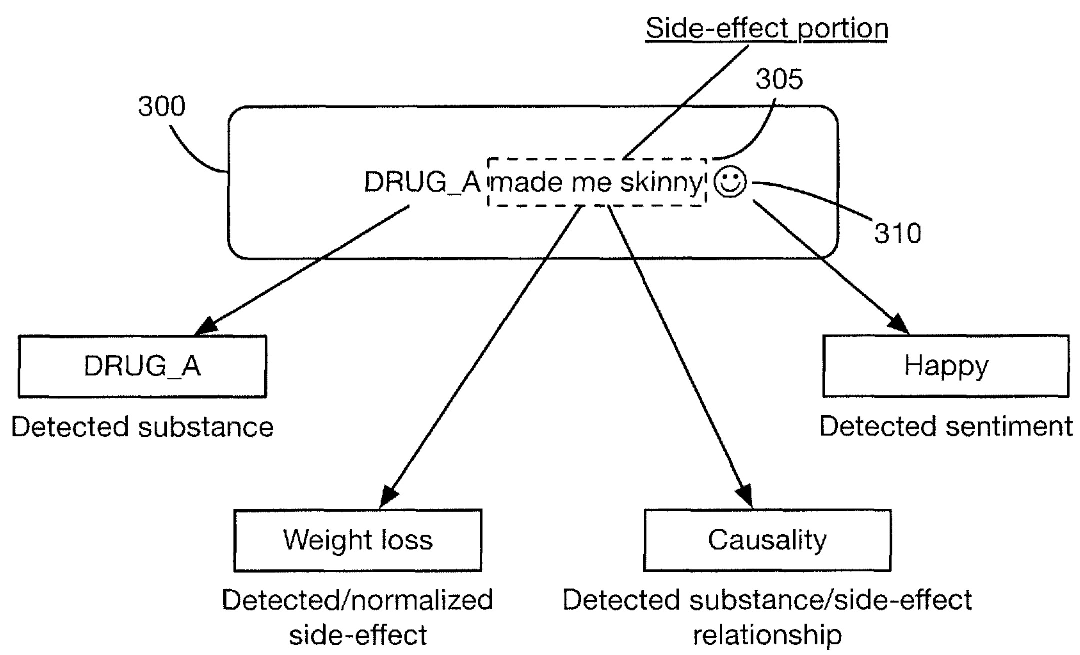
FIG. 3B illustrates various portions of the phrase related to a substance and a possible side-effect associated with the substance.

At block 210, if the comment is determined to be reliable, then the disease symptom recognizer 125 may analyze the comment to identify a portion of the comment associated with a side-effect. In this regard, the side-effect recognizer 125 may utilize a recurrent neural network (RNN) such as a long short-term memory (LSTM) RNN to identify the portion 305 of the comment associated with the side-effect, as illustrated in FIG. 3B. This ability may be enhanced by inputting standard medical descriptions for different side-effects into the LSTM. The standard medical descriptions may be stored in a terms database 127 that is coupled to the LSTM.

Figure 4:
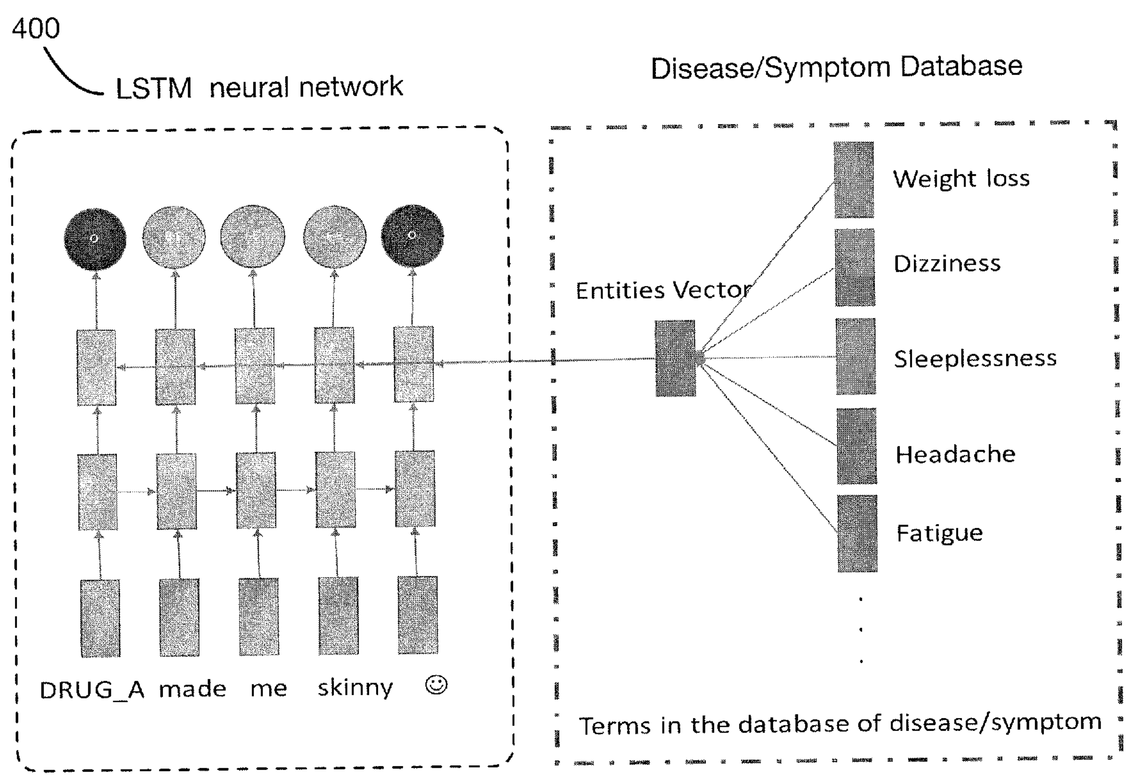
FIG. 4 illustrates the topology of an exemplary long short-term memory (LSTM) recurrent neural network (RNN) for detecting a portion of the phrase associated with a side-effect.
Figure 6:
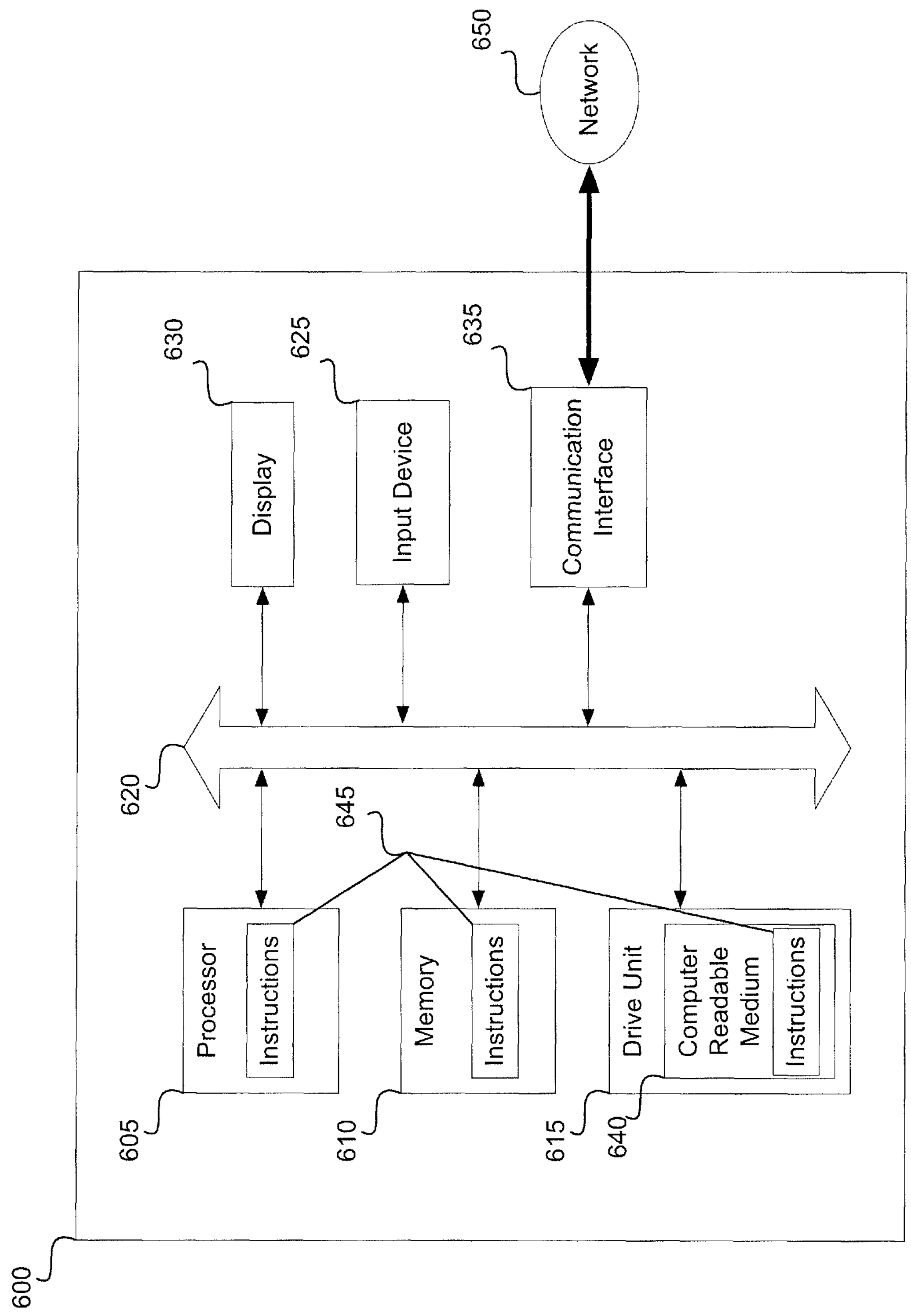
FIG. 6 illustrates an exemplary computer system that may form part of or implement the systems described in the figures or in the following paragraphs.

FIG. 4 illustrates one way in which terms from the terms database 127 may be input into the LSTM. In particular, the LSTM network 400 learns to represent the data regarding disease/symptom from the entire database as a multi-dimensional real value vector. This vector is fed into the LSTM network 400 when learning to classify whether each word in a social media post is related to a disease/symptom. The disease/symptom database vector allows the LSTM to leverage the knowledge about the textual description of diseases/symptoms, when identifying the mentions of diseases/symptoms.

Referring back to FIG. 2, at block 215 the side-effect normalizer 130 may determine a standard/common description associated with the phrase 305 determined at block 210. In this regard, the side-effect normalizer 130 may utilize convolution neural network to map the phrase 305 to a standard medical description stored in the terms database 127. A convolution neural network is a special type of Deep Neural Network that consists of four layers: a convolutional layer, a max pooling layer, a fully connected layer, and a softmax layer. The convolution neural network produces a representation of the text that side-effect in the first 3 layers and then this representation is feed into the softmax layer to map the text to the standard side-effect code stored in the database.

Table 1 illustrates an exemplary pair of phrases to standard medical descriptions that may be determined by the side-effect normalizer 130.

TABLE 1

| Extracted Text | Standard description |
|---|---|
| made me skinny | "Weight loss" |
| feel dizzyyy | "Dizziness" |
| . . . | . . . |

In this example, the side-effect normalizer 130 may determine the standard/common description associated with the phrase 305 to mean "Weight loss."

At block 220, the relationship extractor 135 may determine the substance associated with the phrase 300. In this regard, the relationship extractor 135 may utilize a recurrent neural network configured differently from the RNN described above to identify a portion of the phrase associated with the substance and a portion of the phrase 300 that indicates a relationship between the substance and the side-effect determined above. This RNN learns to identify the relationship between the substance and the side-effect by using the textual information within the phrase 300. In particular, RNN could learn the complex structure of the sentence in the phrase 300, in order to identify the deemed relationship between the substance and the side-effect. For example, identify the relationship as "caused side-effect," when processing the phrase 300 "Have really bad headache after taking DRUG_A."

The relationship extractor 135 may utilize similar techniques to determine the relationship between the determined substance and the side-effect determined at block 215. For example, based on the portion "made me skinny" 305 in the phrase 300, the relationship extractor 135 may determine a causal relationship to exist between the substance and the side-effect. That is, the substance "caused" weight loss. Other relationships might be determined. For example, the relationship extractor 135 may determine that the substance "prevented, enhanced, improved, etc." the side-effect.

At block 225, the emotion detector 140 may attempt to identify a portion of the phrase related to sentiment. For example, the emotion detector 140 may search for emoji 310 or other text indicative of the sentiment of the phrase (e.g., ☺, ;>, LOL, etc.). The emotion detector 140 may utilize a long short-term memory (LSTM) recurrent neural network (RNN) to classify the detected emoji/emoticon or text into one of a group of sentiments types. (I.e., happy, mad, sad, neutral, etc.) Each emoticon has textual description and that textual description expresses the polarity of the corresponding emoticon. The emotion detector 140 utilizes this textual description to predict the polarity of the emoticon. Where a given tweet emoticon is not the only signal of emotion in the emotion detector analyses, the sentiment of the text and the final outcome is the average of emoticon and text sentiment predictions.

At block 230, the processor 150 may generate a record in a substance/side-effect database 128 to relate the substance and relationship determined at block 220 with the side-effect determined at block 215, as illustrated in Table 2.

TABLE 2

| Substance | Relationship | Side-effect | Count |
|---|---|---|---|
| DRUG_A | Causes | Weight loss | 5 |
| DRUG_A | Reduces | Nausea | 1 |
| DRUG_B | Prevents | Vertigo | 10 |
| DRUG_C | Cures | Depression | |
| . . . | . . . | | |

In some implementations, the number of times a particular substance is determined to have a particular relationship with a particular side-effect may be tracked. For example, five phrases from various social media sources 110 may have resulted in a determination that DRUG_A causes weight loss. In this case, the relationship between these terms may have a count of five. Inclusion of the count facilitates determining the most common side-effects associated with a given substance along with other less common side-effects.

The reporting system 145 may facilitate access to the information stored in the substance/side-effect database 128. For example, the reporting system 145 may implement a web server for generating web pages that allows a user of a terminal 115 to access the information. The web pages may include various fields that facilitate searching the substance/side-effect database 128. For example, the fields may allow a user of the terminal 115 to specify a relationship such as "cures" and a side-effect such as "depression" to facilitate retrieving from the substance/side-effect database 128 substances that were determined, based on social media comments, to cure depression.

FIG. 7 illustrates a computer system 600 that may form part of or implement the systems described above. The computer system 600 may include a set of instructions 645 that the processor 605 may execute to cause the computer system 600 to perform any of the operations described above. The computer system 600 may operate as a standalone device or may be connected, e.g., using a network, to other computer systems or peripheral devices.

In a networked deployment, the computer system 600 may operate in the capacity of a server or as a client-user computer in a server-client user network environment, or as a peer computer system in a peer-to-peer (or distributed) network environment. The computer system 600 may also be implemented as or incorporated into various devices, such as a personal computer or a mobile device, capable of executing the instructions 645 (sequential or otherwise) that specify actions to be taken by that machine. Further, each of the systems described may include any collection of subsystems that individually or jointly execute a set, or multiple sets, of instructions to perform one or more computer functions.

The computer system 600 may include one or more memory devices 610 on a bus 620 for communicating information. In addition, code operable to cause the computer system to perform any of the operations described above may be stored in the memory 610. The memory 610 may be a random-access memory, read-only memory, programmable memory, hard disk drive or any other type of memory or storage device.

The computer system 600 may include a display 630, such as a liquid crystal display (LCD), a cathode ray tube (CRT), or any other display suitable for conveying information. The display 630 may act as an interface for the user to see the functioning of the processor 605, or specifically as an interface with the software stored in the memory 610 or in the drive unit 615.

Additionally, the computer system 600 may include an input device 625, such as a keyboard or mouse, configured to allow a user to interact with any of the components of system 600.

The computer system 600 may also include a disk or optical drive unit 615. The disk drive unit 615 may include a computer-readable medium 640 in which the instructions 645 may be stored. The instructions 645 may reside completely, or at least partially, within the memory 610 and/or within the processor 605 during execution by the computer system 600. The memory 610 and the processor 605 also may include computer-readable media as discussed above.

The computer system 600 may include a communication interface 635 to support communications via a network 650. The network 650 may include wired networks, wireless networks, or combinations thereof. The communication interface 635 network may enable communications via any number of communication standards, such as 802.11, 802.12, 802.20, WiMAX, cellular telephone standards, or other communication standards.

Accordingly, the method and system may be realized in hardware, software, or a combination of hardware and software. The method and system may be realized in a centralized fashion in at least one computer system or in a distributed fashion where different elements are spread across several interconnected computer systems. Any kind of computer system or other apparatus adapted for carrying out the methods described herein may be employed.

The method and system may also be embedded in a computer program product, which includes all the features enabling the implementation of the operations described herein and which, when loaded in a computer system, is able to carry out these operations. Computer program in the present context means any expression, in any language, code or notation, of a set of instructions intended to cause a system having an information processing capability to perform a particular function, either directly or after either or both of the following: a) conversion to another language, code or notation; b) reproduction in a different material form.

While methods and systems have been described with reference to certain embodiments, it will be understood by those skilled in the art that various changes may be made and equivalents may be substituted without departing from the scope of the claims. Therefore, it is intended that the present methods and systems not be limited to the particular embodiment disclosed, but that the disclosed methods and systems include all embodiments falling within the scope of the appended claims.

We claim:

1. A system for determining adverse effects associated with a substance, the system comprising:

a side-effect recognizer configured to identify a first portion of received data associated with an adverse effect to thereby determine the adverse effect associated with the received data;

a relationship extractor configured to identify a second portion of the received data associated with a substance and a third portion of the received data that indicates a relationship between the substance and the adverse effect to thereby determine the substance associated with the received data and the relationship between the substance and the adverse effect;

a processor in communication with the side-effect recognizer and the substance relationship extractor that aggregates and relates the adverse effect, substance, and relationship; and a reporting system in communication with the processor that generates a report to convey the relationship between the substance and the adverse effect, wherein the side-effect recognizer is coupled to a terms database that includes a plurality of terms associated with diseases and symptoms, wherein the side-effect recognizer utilizes a recurrent neural network (RNN) to identify the first portion of the received data associated with an adverse effect, wherein the recurrent neural network corresponds to a long short-term memory (LSTM) RNN that corresponds to a real-value multi-dimensional vector that represents knowledge in the database, and wherein the LSTM RNN is configured to learn an effective vector representation of the database when learning to classify whether a word in the received data is related to a disease/symptom, which facilitates leveraging, by the LSTM RNN, textual information about disease and symptom in the database.

2. The system according to claim 1, further comprising a side-effect normalizer, wherein the side-effect normalizer is coupled to the terms database and is configured to select a term in the terms database most closely related to the first portion of the received data, wherein the adverse effect associated with the received data corresponds to the selected term.

3. The system according to claim 1, wherein the relationship extractor utilizes a recurrent neural network (RNN) to identify a second portion of the received data associated with a substance and a third portion of the received data that indicates a relationship between the substance and the adverse effect wherein the RNN corresponds to a long short-term memory (LSTM) RNN.

4. The system according to claim 1, wherein the system retrieves the received data from a source of social media information, wherein the system further comprises a reliability filter that includes a support vector machine configured to assess a reliability of a source of the received data and to categorize the received data as reliable or unreliable.

5. The system according to claim 1, further comprising a sentiment detector configured to identify a third portion of the received data associated with a sentiment and to utilize a long short-term memory (LSTM) RNN to classify the sentiment.

6. A non-transitory computer readable medium that includes instruction code that facilitates determining adverse effects associated with a substance, the instruction code being executable by a machine for causing the machine to perform acts comprising:

controlling a first recurrent neural network (RNN) to identify a first portion of a received data associated with an adverse effect to thereby determine the adverse effect associated with the received data;

controlling a second RNN to identify a second portion of the received data associated with a substance and a third portion of the received data that indicates a relationship between the substance and the adverse effect to thereby determine the substance associated with the received data and the relationship between the substance and the adverse effect;

aggregating and relating the adverse effect, substance, and relationship; and generating a report to convey the relationship between the substance and the adverse effect, wherein the first recurrent neural network corresponds to a long short-term memory (LSTM) recurrent neural network (RNN) that corresponds to a real-value multi-dimensional vector that represents knowledge in the database, and wherein the LSTM RNN is configured to learn an effective vector representation of the database when learning to classify whether a word in the received data is related to a disease/symptom, which facilitates leveraging, by the LSTM RNN, textual information about disease and symptom in the database.

7. The non-transitory computer readable medium according to claim 6, further comprising selecting a term in the terms database most closely related to the first portion of the received data, wherein the adverse effect associated with the received data corresponds to the selected term.

8. The non-transitory computer readable medium according to claim 6, wherein the second recurrent neural network corresponds to a long short-term memory (LSTM) RNN.

9. The non-transitory computer readable medium according to claim 6, further comprising retrieving the received data from a source of social media information and controlling a support vector machine to categorize the received data as reliable or unreliable.

10. The non-transitory computer readable medium according to claim 6, further comprising controlling a long short-term memory (LSTM) RNN to identify a third portion of the received data associated with a sentiment and to classify a sentiment type of the third portion.

11. A method for determining adverse effects associated with a substance, the method comprising:

identifying, by a first recurrent neural network (RNN), a first portion of received data associated with an adverse effect to thereby determine the adverse effect associated with the received data;

identifying, by a second RNN, a second portion of the received data associated with a substance and a third portion of the received data that indicates a relationship between the substance and the adverse effect to thereby determine the substance associated with the received data and the relationship between the substance and the adverse effect;

aggregating and relating the adverse effect, substance, and relationship; and generating a report to convey the relationship between the substance and the adverse effect, wherein the first RNN is coupled to a terms database that includes a plurality of terms associated with diseases and symptoms, wherein the first recurrent neural network corresponds to a long short-term memory (LSTM) RNN that corresponds to a real-value multi-dimensional vector that represents knowledge in the database, and wherein the LSTM RNN is configured to learn an effective vector representation of the database when learning to classify whether a word in the received data is related to a disease/symptom, which facilitates leveraging, by the LSTM RNN, textual information about disease and symptom in the database.

12. The system according to claim 11, further comprising selecting a term in the terms database most closely related to the first portion of the received data, wherein the adverse effect associated with the received data corresponds to the selected term.

13. The system according to claim 11, wherein the second RNN corresponds to a long short-term memory (LSTM) RNN.

14. The system according to claim 11, further comprising retrieving the received data from a source of social media information and categorizing, by a support vector machine, the received data as reliable or unreliable.

15. The system according to claim 11, further comprising identifying, by a long short-term memory (LSTM) RNN, a third portion of the received data associated with a sentiment and to classifying, by the LSTM, a sentiment type of the third portion.

* * * * *